United States Patent
Peterson et al.

(10) Patent No.: US 12,037,429 B2
(45) Date of Patent: Jul. 16, 2024

(54) PROCESS FOR PRODUCING SUPERABSORBENT POLYMER PARTICLES

(71) Applicant: BASF SE, Ludwigshafen (DE)

(72) Inventors: Monte Alan Peterson, Freeport, TX (US); Ruediger Funk, Ludwigshafen (DE); Matthias Weismantel, Ludwigshafen (DE); Juergen Schroeder, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 488 days.

(21) Appl. No.: 17/432,135

(22) PCT Filed: Feb. 21, 2020

(86) PCT No.: PCT/EP2020/054581
§ 371 (c)(1),
(2) Date: Aug. 19, 2021

(87) PCT Pub. No.: WO2020/178044
PCT Pub. Date: Sep. 10, 2020

(65) Prior Publication Data
US 2022/0185924 A1 Jun. 16, 2022

(30) Foreign Application Priority Data
Mar. 1, 2019 (EP) ..................... 19160276

(51) Int. Cl.
| | |
|---|---|
| *B02C 4/42* | (2006.01) |
| *A61L 15/60* | (2006.01) |
| *B01J 20/26* | (2006.01) |
| *B01J 20/28* | (2006.01) |
| *B01J 20/30* | (2006.01) |
| *B02C 4/02* | (2006.01) |
| *B02C 4/28* | (2006.01) |
| *B02C 4/40* | (2006.01) |
| *C08F 2/06* | (2006.01) |
| *C08F 220/06* | (2006.01) |

(52) U.S. Cl.
CPC ............ *C08F 220/06* (2013.01); *A61L 15/60* (2013.01); *B01J 20/267* (2013.01); *B01J 20/28004* (2013.01); *B01J 20/3021* (2013.01); *B02C 4/02* (2013.01); *B02C 4/286* (2013.01); *B02C 4/40* (2013.01); *C08F 2/06* (2013.01); *B01J 2220/68* (2013.01)

(58) Field of Classification Search
CPC .................. B01J 2220/68; B01J 20/267; B01J 20/28004; B01J 20/3021; C08F 2/06; C08F 220/06; B02C 4/02; B02C 4/286; B02C 4/40; A61L 15/60
See application file for complete search history.

(56) References Cited

U.S. PATENT DOCUMENTS

| | | | |
|---|---|---|---|
| 9,550,843 B2 | 1/2017 | Matsumoto et al. | |
| 2012/0283401 A1* | 11/2012 | Funk ...................... | C08F 6/008 |
| | | | 526/181 |
| 2012/0302711 A1 | 11/2012 | Funk et al. | |

FOREIGN PATENT DOCUMENTS

| | | |
|---|---|---|
| EP | 2689852 A2 | 1/2014 |
| JP | S5329392 A | 3/1978 |
| JP | 2013-076073 A | 4/2013 |
| WO | WO-2014/084281 A1 | 6/2014 |

OTHER PUBLICATIONS

Graham, et al., "Chapter 3: Commercial Processes for the Manufacture of Superabsorbent Polymers", Modern Superabsorbent Polymer Technology, ed. Buchholz, et al., 2nd Edition, 1998, pp. 69-117.
International Application No. PCT/EP2020/054581, International Search Report and Written Opinion, mailed May 25, 2020.

* cited by examiner

*Primary Examiner* — Nahida Sultana
*Assistant Examiner* — Jamel M Nelson
(74) *Attorney, Agent, or Firm* — MARSHALL, GERSTEIN & BORUN LLP

(57) ABSTRACT

The invention relates to a process for producing superabsorbent polymer particles, comprising polymerization of a monomer solution, drying the resulting polymer gel and grinding the dried polymer gel with a roll mill, wherein the rolls of the roll mill are cleaned by reducing the feed rate to the roll mill, and if the deflection and/or the power consumption increases above a setpoint, operating the roll mill with reduced feed, and increasing the feed rate to the roll mill.

14 Claims, No Drawings

PROCESS FOR PRODUCING SUPERABSORBENT POLYMER PARTICLES

CROSS-REFERENCE TO RELATED APPLICATIONS

This is the U.S. national phase of International Application No. PCT/EP2020/054581, filed Feb. 21, 2020, which claims the benefit of European Patent Application No. 19160276.2, filed on Mar. 1, 2019.

The invention relates to a process for producing superabsorbent polymer particles, comprising polymerization of a monomer solution, drying the resulting polymer gel and grinding the dried polymer gel with a roll mill, wherein the rolls of the roll mill are cleaned by reducing the feed rate to the roll mill, and if the deflection and/or the power consumption increases above a setpoint, operating the roll mill with reduced feed, and increasing the feed rate to the roll mill.

Superabsorbent polymer particles are used to produce diapers, tampons, sanitary napkins and other hygiene articles, but also as water-retaining agents in market gardening. The superabsorbent polymer particles are often also referred to as "absorbent resin", "superabsorbent", "superabsorbent polymers", "absorbent polymers", "absorbent gelling materials", "hydrophilic polymers" or "hydrogels".

Commercial superabsorbent polymer particles are polymers of partially neutralized acrylic acid as described in the monograph "Modern Superabsorbent Polymer Technology", F. L. Buchholz and A. T. Graham, Wiley-VCH, 1998, pages 69 to 103.

It was an object of the present invention to provide an improved process for producing superabsorbent polymer particles, especially an improved cleaning of the roll mills that are used for grinding of the dried polymer gel.

The object was achieved by a process for producing superabsorbent polymer particles, comprising polymerization of a monomer solution, comprising
   a) partially neutralized acrylic acid,
   b) at least one crosslinker, and
   c) at least one initiator,
drying the resulting polymer gel and grinding the dried polymer gel with a roll mill, wherein the rolls of the roll mill are cleaned by the following procedure
   i) determining the deflection and/or the power consumption of the roll mill,
   ii) reducing the feed rate to the roll mill or stopping the feed to the roll mill, if the deflection and/or the power consumption increases above a setpoint,
   iii) optionally increasing the gap width between the rolls of the roll mill,
   iv) operating the roll mill with reduced feed rate or stopped feed,
   v) optionally reducing the gap width between the rolls of the roll mill,
   vi) optionally operating roll mill with reduced gap width until the deflection and/or the power consumption decreases below the setpoint,
   vii) optionally increasing the gap width between the rolls of the roll mill to the gap width prior to step ii), and
   viii) increasing the feed rate to the roll mill to the feed rate prior to step ii) or re-starting the feed to the roll mill,
wherein the gap width between the rolls of the roll mill must be reduced in step v) if the feed to the roll mill was stopped in step ii) and the gap width between the rolls of the roll mill was increased in step iii),
and classifying the resulting polymer particles.

The setpoint of the deflection bases on vibrations of the rolls that indicates fouling on the rolls. The setpoint of the deflection is, for example, 5% higher than the deflection with clean rolls at the same feed rate.

The setpoint of the power consumption bases on a power consumption of the roll mill that indicates fouling on the rolls. The setpoint of the power consumption of the roll mill is, for example, 5% higher than the power consumption of the roll mill with clean rolls at the same feed rate.

The roll mill is a single- or multistage roll mill, preferably a two- or three-stage roll mill. Each stage of a roll mill consists of a pair of rolls, wherein one roll is fixed and the other roll is non-fixed. The non-fixed roll can deflect in horizontal direction, if elastic material, i.e. incomplete dried polymer particles, sticks on a roll and the elastic material is larger than the gap width between the rolls. That deflection causes vibration of the non-fixed roll.

In a first embodiment of the present invention the rolls of the roll mill are cleaned by the following procedure
   i) determining the deflection of the rolls and/or the power consumption of the roll mill,
   ii) reducing the feed rate to the roll mill, if the deflection and/or the power consumption increases above a setpoint,
   iv) operating the roll mill with reduced feed rate until the deflection and/or the power consumption decreases below the setpoint,
   viii) increasing the feed rate to the roll mill to the feed rate prior to step ii).

The feed rate to the roll mill is reduced in step ii), if the deflection and/or the power consumption is above the setpoint preferably for at least 0.5 seconds, more preferably for at least 1 seconds, most preferably for at least 1.5 seconds.

The feed rate to the roll mill is increased in step viii), if the deflection and/or the power consumption is below the setpoint preferably for at least 1.5 seconds, more preferably for at least 2.0 seconds, most preferably for at least 2.5 seconds.

The feed rate to the roll mill in step ii) may be stepwise reduced and/or the feed rate to the roll mill in step viii) may be stepwise increased. A stepwise reduction of the feed rate means that the roll mill operates with the reduced feed rate for a pre-defined time. If the deflection and/or the power consumption are still above the setpoint, the feed rate is reduced again. A stepwise increase of the feed rate means that the roll mill operates with the increased feed rate for a pred-defined time. If the deflection and/or the power consumption are still below the setpoint, the feed rate is increased again.

The pre-defined time is preferably from 1 to 30 seconds, more preferably from 3 to 20 seconds, most preferably from 5 to 15 seconds.

The feed rate to the roll mill in step ii) is stepwise reduced by preferably 2 to 20% per step, more preferably 5 to 15% per step, most preferably 7 to 10% per step, based on the feed rate prior to step ii).

The minimum feed rate to the roll mill in step iv) is preferably at least 25%, more preferably at least 30%, most preferably at least 35%, based on the feed rate prior to step ii).

The feed rate to the roll mill in step viii) is stepwise increased by preferably 0.5 to 10% per step, most preferably 1.0 to 5% per step, most preferably 1.5 to 5% per step, based on the feed rate prior to step ii).

The present invention is based on the finding that the rolls of the roll mill can be cleaned by reduction of the feed rate.

In a second embodiment of the present invention the rolls of the roll mill are cleaned by the following procedure
  i) determining the deflection of the rolls and/or the power consumption of the roll mill,
  ii) stopping the feed to the roll mill, if the deflection and/or the power consumption increases above a setpoint,
  iv) operating the roll mill with stopped feed,
  v) reducing the gap width between the rolls of the roll mill,
  vi) operating roll mill with reduced gap width until the deflection and/or the power consumption decreases below the setpoint,
  vii) increasing the gap width between the rolls of the roll mill to the gap width prior to step ii), and
  viii) re-starting the feed rate to the roll mill.

The feed rate to the roll mill is stopped in step ii), if the deflection and/or the power consumption is above the setpoint preferably for at least 0.5 seconds, more preferably for at least 1 seconds, most preferably for at least 1.5 seconds.

The roll mill operates with stopped feed in step iv) for preferably at least 0.5 minutes, more preferably at least 1.0 minutes, most preferably at least 2.0 minutes.

The gap width between the rolls of the roll mill in step v) is reduced to preferably less than 0.1 mm, more preferably less than 0.05 mm, most preferably less than 0.02 mm.

The feed rate to the roll mill is increased in step viii), if the deflection and/or the power consumption is below the setpoint preferably for at least 1.5 seconds, more preferably for at least 2.0 seconds, most preferably for at least 2.5 seconds.

The present invention is based on the finding that the rolls of the roll mill can be cleaned by stopping the feed and reducing the gap width as low as possible. Under these conditions, incompletely dried polymer particles can be completely dried and easily be removed from the rolls.

In a third embodiment of the present invention the rolls of the roll mill are cleaned by the following procedure
  i) determining the deflection of the rolls and/or the power consumption of the roll mill,
  ii) stopping the feed to the roll mill, if the deflection and/or the power consumption increases above a setpoint,
  iii) increasing the gap width between the rolls of the roll mill,
  iv) operating the roll mill with stopped feed,
  v) reducing the gap width between the rolls of the roll mill,
  vi) operating roll mill with reduced gap width until the deflection and/or the power consumption decreases below the setpoint,
  vii) increasing the gap width between the rolls of the roll mill to the gap width prior to step ii), and
  viii) re-starting the feed rate to the roll mill.

The feed rate to the roll mill is stopped in step ii), if the deflection and/or the power consumption is above the setpoint preferably for at least 0.5 seconds, more preferably for at least 1 seconds, most preferably for at least 1.5 seconds.

The gap width between the rolls of the roll mill in step iii) is increased to preferably at least 1.0 mm, more preferably at least 1.5 mm, most preferably at least 2.0 mm.

The roll mill operates with stopped feed in step iv) for preferably at least 0.5 minutes, more preferably at least 1.0 minutes, most preferably at least 2.0 minutes.

The gap width between the rolls of the roll mill in step v) is reduced to preferably less than 0.1 mm, more preferably less than 0.05 mm, most preferably less than 0.02 mm.

The feed rate to the roll mill is increased in step viii), if the deflection and/or the power consumption is below the setpoint preferably for at least 1.5 seconds, more preferably for at least 2.0 seconds, most preferably for at least 2.5 seconds.

The present invention is based on the finding that the rolls of the roll mill can be cleaned by stopping the feed and reducing the gap width as low as possible. Under these conditions, incompletely dried polymer particles can be completely dried and easily be removed from the rolls. Increasing the gap width after stopping the feed removes quickly polymer particles from the roll mill so that the next steps can start earlier.

The production of the superabsorbent polymer particles is described in detail hereinafter:

The superabsorbent polymer particles are produced by polymerizing a monomer solution and are typically water-insoluble.

Acrylic acid typically comprises polymerization inhibitors, preferably hydroquinone monoethers, as storage stabilizers.

The monomer solution comprises preferably up to 250 ppm by weight, preferably at most 150 ppm by weight, more preferably at most 100 ppm by weight, and preferably at least 10 ppm by weight, more preferably at least 30 ppm by weight and especially around 50 ppm by weight, of hydroquinone monoether, based in each case on acrylic acid prior to neutralization. For example, the monomer solution can be prepared by using acrylic acid with an appropriate content of hydroquinone monoether.

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of acrylic acid. In addition, polyvalent metal salts which can form coordinate bonds with at least two acid groups of acrylic acid are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallyl ammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

The amount of crosslinker b) is preferably 0.05 to 1.5% by weight, more preferably 0.1 to 1% by weight and most preferably 0.3 to 0.6% by weight, based in each case on acrylic acid prior to neutralization. With rising crosslinker content, the centrifuge retention capacity (CRC) falls and the absorption under a pressure of $21.0 \text{ g/cm}^2$ passes through a maximum.

The initiators c) used may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/ sodium bisulfite. Preference is given to using mixtures of thermal initiators and redox initiators, such as sodium peroxodisulfate/hydrogen peroxide/ascorbic acid. However, the reducing component used is preferably disodium 2-hydroxy-2-sulfonatoacetate or a mixture of disodium 2-hydroxy-2-sulfinatoacetate, disodium 2-hydroxy-2-sulfonatoacetate and sodium bisulfite. Such mixtures are obtainable as Brüggolite® FF6 and Brüggolite® FF7 (Brüggemann Chemicals; Heilbronn; Germany).

Typically, an aqueous monomer solution is used. The water content of the monomer solution is preferably from 40 to 75% by weight, more preferably from 45 to 70% by weight and most preferably from 50 to 65% by weight. It is also possible to use monomer suspensions, i.e. monomer solutions with excess sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

For better control of the polymerization reaction, it is optionally possible to add all known chelating agents to the monomer solution or suspension or to the raw materials thereof. Suitable chelating agents are, for example, phosphoric acid, diphosphoric acid, triphosphoric acid, polyphosphoric acid, citric acid, tartaric acid, or salts thereof.

The monomer solution is polymerized. Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on the belt is described, for example, in DE 38 25 366 A1 and U.S. Pat. No. 6,241,928. Polymerization in a belt reactor forms a polymer gel which must be comminuted in a further process step, for example in an extruder or kneader.

To improve the drying properties, the comminuted polymer gel obtained by means of a kneader can additionally be extruded.

The acid groups of the resulting polymer gels have typically been partially neutralized. Neutralization is carried out at the monomer stage. This is typically accomplished by mixing in the neutralizing agent as an aqueous solution or preferably also as a solid. The degree of neutralization is preferably from 50 to 85 mol %, more preferably from 60 to 80 mol % and most preferably from 65 to 75 mol %, for which the customary neutralizing agents can be used, preferably alkali metal hydroxides, alkali metal oxides, alkali metal carbonates or alkali metal hydrogen carbonates and mixtures thereof. Instead of alkali metal salts, it is also possible to use ammonium salts. Particularly preferred alkali metals are sodium and potassium, but very particular preference is given to sodium hydroxide, potassium hydroxide and mixtures thereof.

The resulting polymer gel is dried. The driers are not subject to any restriction. However, the drying of the polymer gel is preferably performed with a belt drier until the residual moisture content is preferably 0.5 to 10% by weight, more preferably 1 to 7% by weight and most preferably 2 to 5% by weight, the residual moisture content being determined by EDANA recommended test method No. WSP 230.2 (05) "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent grinding steps, undesirably large amounts of polymer particles with an excessively low particle size are obtained ("fines"). The solids content of the gel before the drying is preferably from 25 to 90% by weight, more preferably from 35 to 70% by weight and most preferably from 40 to 60% by weight. However, a fluidized bed drier or a paddle drier may optionally also be used for drying purposes.

Subsequently, the dried polymer gel is ground and classified.

The mean particle size of the polymer particles removed as the product fraction is preferably at least 200 µm, more preferably from 250 to 600 µm and very particularly from 300 to 500 µm. The mean particle size of the product fraction may be determined by means of EDANA recommended test method No. WSP 220.2 (05) "Particle Size Distribution", where the proportions by mass of the screen fractions are plotted in cumulated form and the mean particle size is determined graphically. The mean particle size here is the value of the mesh size which gives rise to a cumulative 50% by weight.

To improve the properties, the polymer particles may subsequently be thermally surface post-crosslinked. Suitable surface post-crosslinkers are compounds which comprise groups which can form covalent bonds with at least two acid groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or #-hydroxyalkyl amides, as described in DE 102 04 938 A1 and U.S. Pat. No. 6,239,230.

The amount of surface post-crosslinker is preferably 0.001 to 2% by weight, more preferably 0.02 to 1% by weight and most preferably 0.05 to 0.2% by weight, based in each case on the polymer particles.

In a preferred embodiment of the present invention, polyvalent cations are applied to the particle surface in addition to the surface post-crosslinkers before, during or after the surface post-crosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, hydroxide, sulfate, hydrogen sulfate, carbonate, hydrogen carbonate, nitrate, phosphate, hydrogen phosphate, dihydrogen phosphate and carboxylate, such as acetate and lactate. Aluminum hydroxide, aluminum sulfate and aluminum lactate are preferred. Apart from metal salts, it is also possible to use polyamines as polyvalent cations.

The amount of polyvalent cation used is, for example, 0.001 to 1.5% by weight, preferably 0.005 to 1% by weight and more preferably 0.02 to 0.8% by weight, based in each case on the polymer particles.

The surface post-crosslinking is typically performed in such a way that a solution of the surface post-crosslinker is sprayed onto the dried polymer particles. After the spray application, the polymer particles coated with surface post-crosslinker are dried thermally, and the surface post-crosslinking reaction can take place either before or during the drying.

The spray application of a solution of the surface post-crosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface post-crosslinker solution in a fluidized bed.

The surface post-crosslinkers are typically used in the form of an aqueous solution. The penetration depth of the surface post-crosslinker into the polymer particles can be adjusted via the content of non-aqueous solvent and total amount of solvent.

The thermal surface post-crosslinking is preferably performed in contact driers, more preferably paddle driers, most preferably disk driers. Suitable driers are, for example, Hosokawa Bepex® Horizontal Paddle Dryer (Hosokawa Micron GmbH; Leingarten; Germany), Hosokawa Bepex® Disc Dryer (Hosokawa Micron GmbH; Leingarten; Germany) and Nara Paddle Dryer (NARA Machinery Europe; Frechen; Germany). Moreover, fluidized bed driers may also be used.

The thermal surface post-crosslinking can be affected in the mixer itself, by heating the jacket or blowing in warm air. Equally suitable is a downstream drier, for example a shelf drier, a rotary tube oven or a heatable screw. It is particularly advantageous to effect mixing and drying in a fluidized bed drier.

Preferred surface post-crosslinking temperatures are in the range of 100 to 250° C., preferably 110 to 230° C., more preferably 120 to 210° C. and most preferably 130 to 190° C. The preferred residence time at this temperature in the reaction mixer or drier is preferably at least 10 minutes, more preferably at least 20 minutes, most preferably at least 30 minutes, and typically at most 60 minutes.

Subsequently, the surface post-crosslinked polymer particles can be classified again, excessively small and/or excessively large polymer particles being removed and recycled into the process.

To further improve the properties, the surface post-crosslinked polymer particles can be coated or remoisturized.

The remoisturizing is preferably performed at 30 to 80° C., more preferably at 35 to 70° C., most preferably at 40 to 60° C. At excessively low temperatures, the superabsorbent polymer particles tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for improving the free swell rate and the saline flow conductivity (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosile® 200, or precipitated silica, such as Sipernat® D17, and surfactants, such as Span® 20.

The present invention further provides hygiene articles, comprising superabsorbent polymer particles prepared according to the inventive process.

EXAMPLES

Preparation of the Superabsorbent Polymer Particles

Example 1

By continuously mixing deionized water, 48% by weight sodium hydroxide solution and acrylic acid, an acrylic acid/sodium acrylate solution was prepared, such that the degree of neutralization corresponds to 72.4 mol %. The solids content of the monomer solution was 40.0% by weight.

The monomer solution was further cooled. Next, 3-tuply ethoxylated glycerol triacrylate was added as crosslinker to the monomer solution. The amount of crosslinker was 1.43 kg per t of monomer solution.

The free-radical polymerization was initiated by adding 1.31 kg of a 0.25% by weight aqueous hydrogen peroxide solution, 3.00 kg of a 30% by weight aqueous sodium peroxodisulfate solution, and 0.98 kg of a 1% by weight aqueous ascorbic acid solution, each based per t of monomer solution. The peroxides were added to the monomer solution.

The throughput of the monomer solution was 21 t/h. The monomer solution had a temperature of 26° C. at the feed.

The components (monomer solution and aqueous ascorbic acid solution) were metered continuously into a continuous kneader reactor with a capacity of 6.3 m$^3$ (LIST AG, Arisdorf, Switzerland).

Between the addition point for the crosslinker and the addition points of the peroxides, the monomer solution was inertized with nitrogen.

After approx. 50% of the residence time in the polymerization reactor, a metered addition of fines (1270 kg/h), which were obtained from the production process by grinding and screening, to the reactor additionally took place. The residence time of the reaction mixture in the reactor was 15 minutes.

The resulting polymer gel was placed onto a belt dryer. On the belt dryer, an air/gas mixture flowed continuously around the polymer gel and dried it.

The dried polymer gel was ground by means of a two-stage roll mill (model WMC152; Neuhaus Neotec Maschinen und Anlagenbau GmbH; Ganderkesee; Germany). The rolls have a length of 1,500 mm and a diameter of 250 mm. The gap of the upper rolls was in the range from 0.3 to 0.5 mm. The tip speed of the upper rolls was in the range from 5.8 to 8.1 m/s. The gap of the lower rolls was in the range from 0.1 to 0.2 mm. The tip speed of the lower rolls was in the range from 7.0 to 10.0 m/s. The feed had a temperature of 40 to 60° C. and moisture content of 1 to 3% by weight. The feed rate was 23.9% (the reading of the DCS corresponds to approximately 2,500 kg/h).

The deflection of the rolls was approx. 19.1% (100% corresponds to the maximum possible deflection of the non-fixed roll) and the power consumption of the rolls was approx. 28.8 A.

The ground polymer was screened off to a particle size fraction of 150 to 850 μm.

Cleaning of the Roll Mill

Example 2

The roll mill in Example 1 was cleaned by the first embodiment of the present invention. The setpoint for the deflection was 21.0%. The setpoint for the power consumption was 31.0 A. Both conditions must be fulfilled for starting the cleaning procedure.

The feed rate was stepwise reduced, if deflection and power consumption were above the setpoint for 2.0 seconds. Then, the feed rate was reduced by 2.0% (8.3% based on the feed rate prior to the cleaning of the roll mill) per step. The time between two steps was 10.0 seconds.

The minimum feed rate was 10% (41.8% based on the feed rate prior to the cleaning of the roll mill).

The feed rate was stepwise increased to a feed rate of 23.9%, if deflection and power consumption were below the setpoint for 3.0 seconds. Then, the feed rate was increased by 0.5% (2.1% based on the feed rate prior to the cleaning of the roll mill) per step. The time between to steps was 10.0 seconds.

The invention claimed is:

1. A process for producing superabsorbent polymer particles, comprising polymerizing a monomer solution, comprising
    a) partly neutralized acrylic acid,
    b) at least one crosslinker, and
    c) at least one initiator,
    drying a resulting polymer gel and grinding a resulting dried polymer gel with a roll mill, wherein rolls of the roll mill are cleaned by the following procedure
    i) determining a deflection of the rolls and/or a power consumption of the roll mill,
    ii) reducing a feed rate to the roll mill or stopping a feed to the roll mill, if the deflection and/or the power consumption increases above a setpoint,
    iii) optionally increasing a gap width between the rolls of the roll mill,
    iv) operating the roll mill with reduced feed rate or stopped feed,
    v) optionally reducing the gap width between the rolls of the roll mill,
    vi) optionally operating roll mill with reduced gap width until the deflection and/or the power consumption decreases below the setpoint,
    vii) optionally increasing the gap width between the rolls of the roll mill to the gap width prior to step ii), and
    viii) increasing the feed rate to the roll mill to the feed rate prior to step ii) or re-starting the feed to the roll mill,
    wherein the gap width between the rolls of the roll mill are reduced in step v) if the feed to the roll mill was stopped in step ii) and the gap width between the rolls of the roll mill was increased in step iii), and classifying the resulting polymer particles.

2. The process according to claim 1, wherein the rolls of the roll mill are cleaned by the following procedure
    i) determining the deflection of the rolls and/or the power consumption of the roll mill,
    ii) reducing the feed rate to the roll mill, if the deflection and/or the power consumption increases above a setpoint,
    iv) operating the roll mill with reduced feed rate until the deflection and/or the power consumption decreases below the setpoint,
    viii) increasing the feed rate to the roll mill to the feed rate prior to step ii).

3. The process according to claim 2, wherein the feed rate to the roll mill in step ii) is stepwise reduced and/or the feed rate to the roll mill in step viii) is stepwise increased.

4. The process according to claim 2, wherein the feed rate to the roll mill in step ii) is stepwise reduced by 2 to 20% per step, based on the feed prior to step ii).

5. The process according to claim 2, wherein the feed rate to the roll mill in step iv) is at least 25%, based on the feed prior to step ii).

6. The process according to claim 2, wherein the feed rate to the roll mill in step viii) is stepwise increased by 0.5 to 10% per step, based on the feed prior to step ii).

7. The process according to claim 1, wherein the rolls of the roll mill are cleaned by the following procedure
    i) determining the deflection of the rolls and/or the power consumption of the roll mill,
    ii) stopping the feed to the roll mill, if the deflection and/or the power consumption increases above a setpoint,
    iv) operating the roll mill with stopped feed,
    v) reducing the gap width between the rolls of the roll mill,
    vi) operating roll mill with reduced gap width until the deflection and/or the power consumption decreases below the setpoint,
    vii) increasing the gap width between the rolls of the roll mill to the gap width prior to step ii), and
    viii) re-starting the feed rate to the roll mill.

8. The process according to claim 7, wherein the roll mill operates with stopped feed in step iv) for at least 2.0 minutes.

9. The process according to claim 7, wherein the gap width between the rolls of the roll mill in step v) is reduced to less than 0.02 mm.

10. The process according to claim 1, wherein the rolls of the roll mill are cleaned by the following procedure
    i) determining the deflection of the rolls and/or the power consumption of the roll mill,
    ii) stopping the feed to the roll mill, if the deflection and/or the power consumption increases above a setpoint,
    iii) increasing the gap width between the rolls of the roll mill,
    iv) operating the roll mill with stopped feed,
    v) reducing the gap width between the rolls of the roll mill,
    vi) operating roll mill with reduced gap width until the deflection and/or the power consumption decreases below the setpoint,
    vii) increasing the gap width between the rolls of the roll mill to the gap width prior to step ii), and
    viii) re-starting the feed rate to the roll mill.

11. The process according to claim 10, wherein the gap width between the rolls of the roll mill in step iii) is increased to at least 2.0 mm.

12. The process according to claim 10, wherein the roll mill operates with stopped feed in step iv) for at least 2.0 minutes.

13. The process according to claim 10, wherein the gap width between the rolls of the roll mill in step v) is reduced to less than 0.02 mm.

14. The process according to claim 1, wherein the roll mill is a multi-stage roll mill.

\* \* \* \* \*